United States Patent [19]

Kelly et al.

[11] 4,041,111

[45] Aug. 9, 1977

[54] PHOSPHONATE MONOESTERS AND METHOD OF PREPARATION

[75] Inventors: Susan J. Kelly, Lafayette; Larry G. Butler, West Lafayette, both of Ind.

[73] Assignee: Purdue Research Foundation, West Lafayette, Ind.

[21] Appl. No.: 555,097

[22] Filed: Mar. 4, 1975

[51] Int. Cl.$^2$ .............................................. C07F 9/40
[52] U.S. Cl. ...................... 260/954; 195/103.5 R; 260/958; 260/961; 260/973; 260/983; 260/987; 260/990
[58] Field of Search ............. 260/954, 958, 961, 973, 260/983, 987, 990

[56] References Cited

U.S. PATENT DOCUMENTS

| | | | |
|---|---|---|---|
| 2,329,707 | 9/1943 | Farrington et al. | 260/958 X |
| 2,784,208 | 3/1957 | Ries | 260/961 |
| 2,908,708 | 10/1959 | Beach | 260/961 X |
| 3,019,249 | 1/1962 | Gunderloy | 260/961 X |
| 3,051,740 | 8/1962 | Abramo et al. | 260/961 X |
| 3,268,629 | 8/1966 | Cherbuliez et al. | 260/961 X |
| 3,699,193 | 10/1972 | Melton | 260/990 X |
| 3,896,163 | 7/1975 | Jacques | 260/990 X |
| 3,897,486 | 7/1975 | Jacques | 260/990 X |

FOREIGN PATENT DOCUMENTS

| | | | |
|---|---|---|---|
| 327,209 | 3/1972 | U.S.S.R. | 260/961 |

OTHER PUBLICATIONS

Houben-Weyl, Methoden der Organischen Chemie, Dec. 1, 1963 pp. 417 and 408 to 414.
Petrov et al. Chemical Abstracts, vol. 63 (1965) 4327.
Dickey, Chemical Abstracts, vol. 46 (1952) 10632.
Burger et al. Chemical Abstracts, vol. 51 (1957) 16331.
Feiser et al. Advanced Organic Chemistry, Reinhold Publishing (New York) 1961, p. 822.

*Primary Examiner*—Richard L. Raymond
*Attorney, Agent, or Firm*—John R. Nesbitt

[57] ABSTRACT

Synthesis of phosphonate monoesters, as well as the use of such monoesters as substrates for enzymes which normally hydrolyze phosphodiester linkages, and a method for distinguishing between Type I and Type II phosphodiesterase enzymes using such monoesters as substrates are disclosed herein. Monoesters of phosphonic acids are prepared by the displacement of chloride from an appropriate phosphonic acid dichloride by a phenol or alcohol with pyridine as the solvent, reacting the same and then removing the solvent, after which the remaining ester chloride and dichloride are hydrolyzed by addition of water. The acid and ester are then separated and the acid-free ester is taken up in a polar organic solvent and precipitated as a salt by the addition of aqueous base, with the product then being filtered, washed with fresh acetone, dried and then stored until needed. The thus formed phosphonate monoesters are shown to be effective for use as substrate for phosphodiesterase of the Type I specificity and are shown to be ineffective for use as substrates for phosphodiesterase of the Type II specificity. The type of phosphodiesterase is therefore determined by the amount of activity against phosphonate monoesters.

6 Claims, No Drawings

PHOSPHONATE MONOESTERS AND METHOD OF PREPARATION

The invention described herein was made in the course of, or under, a grant from the National Institute of Health, Department of Health, Education, and Welfare, Grants No. GM46404(LGB) and GM1195(SJK).

FIELD OF THE INVENTION

This invention relates to phosphonate monoesters, and more particularly relates to the synthesis of phosphonate monoesters and to the use and method of using the same as a substrate and for distinguishing between specified types of phosphodiesterase enzymes.

BACKGROUND OF THE INVENTION

Phosphonate monoesters are known to be closely related to phosphate diesters which are known to be important components of every living cell. In addition, phosphonate monoesters have heretofore been synthesized, normally by one of two general methods, the first of which includes reaction of a phosphonic dichloride under limiting conditions of alcohol, to reduce the possibility of diester formation, with subsequent hydrolysis of the remaining chloride, and the second of which includes formation of the diester with subsequent hydrolysis to the monoester in aqueous or alcoholic alkali.

With respect to the reaction of a phosphonic dichloride, attention is invited to the work of Fild, M. and Schmutzler, R. appearing in 1972 in Organic Phosphorus Compounds, Volume 4, G. M. Kosolapoff and L. Maier, Ed., Wiley-Interscience, New York, Chapter 8. With respect to reducing the possibility of diester formation, attention is invited to the work of Michaelis, A. and Kammerer, K. appearing in 1875 in Ber., Volume 8, page 1307, and the work of Keay, L. appearing in 1965 in the Canadian Journal of Chemistry, Volume 43, page 2637.

With respect to the formation of the diester, this has been achieved by procedures heretofore described by Kosolapoff, G. M. in 1950 in Organophosphorus Compounds, Wiley, New York, Chapter 7. In addition, methods analogous to the preparation of phosphate triesters have been suggested for formation of the diester (see the work of Cherbuliez, E. appearing in 1973 in Organic Phosphorus Compounds, Volume 6, Wiley-Interscience, New York, Chapter 15), with subsequent hydrolysis to the monoester in aqueous or alcoholic alkali being suggested by Behrman, E. J., Biallas, M. J., Brass, H. J., Edwards, J. O., and Isaks, M., in 1970 in the Journal of Organic Chemistry, Volume 35, page 3063.

Since phosphates are major constitutents of every living cell and constitute the structural basis of the nucleic acids, with phosphate diesters being among the most important chemical bonds known, enzymes which are capable of making or breaking such phosphodiester bonds are of considerable importance. Although many enzymes which hydrolyze phosphodiester bonds are known, those which hydrolyze nucleic acids sequentially from a terminus fit into one of two broad classifications, or types, as observed by Razzell, W. E., in 1967 in Experienta, Volume 23, page 321.

While several methods have been utilized for assaying phosphodiesterase activity, none of the methods have been found to be fully suitable in combining convenience, economy and specificity. This has been due, at least in part, to the fact that the natural nucleotide substrates of these enzymes have properties which change so little on hydrolysis that somewhat sophisticated equipment and techniques are required in order to quantitate the reaction. Properties such as increase in absorbance of uv light, decrease in viscosity, and increase in acid-soluble nucleotides have been used in assays. Synthetic chromogenic esters of nucleotides, such as 4-nitrophenyl esters of 5'-thymidine monophosphate have been employed as phosphodiesterase substrates, with spectrophotometric detection of the 4-nitrophenol produced on hydrolysis, but these materials are too expensive to be widely used. An inexpensive chromogenic phosphate diester, bis-(4-nitrophenyl) phosphate, has been widely used but most phosphodiesterases hydrolyze it very ineffectively, if at all, as reported by Razzell, W. E. and Khorana, H. G. in 1959 in the Journal of Biological Chemistry, Volume 234, page 2105. Thus, a need has existed for a convenient and inexpensive phosphodiesterase substrate.

SUMMARY OF THE INVENTION

This invention provides for improved synthesis of phosphonate monoesters, as well as the novel use and method for using such monoesters as substrates and for distinguishing between specified types of phosphodiesterase enzymes. In accomplishing the desired ends, a convenient and inexpensive phosphodiesterase substrate has been provided as well as a plurality of novel phosphonate monoesters that are particularly well suited for use as such substrates, and are usable to distinguish between Types I and II phosphodiesterase enzymes.

It is therefore an object of this invention to provide novel synthesis of phosphonate monoesters.

It is another object of this invention to provide novel phosphonate monoesters useful as substrates for enzymes which hydrolyze phosphodiester linkages.

It is still another object of this invention to provide phosphonate monoesters useful as substrates to distinguish between specified types of phosphodiesterase enzymes.

It is yet another object of this invention to provide an improved method for distinguishing between specified types of phosphodiesterase enzymes.

It is another object of this invention to provide an improved phosphodiesterase substrate that is both convenient and inexpensive.

With these and other objects in view which will become apparent to one skilled in the art as the description proceeds, this invention resides in the novel formulations, uses and methods substantially as hereinafter described, and more particularly defined by the appended claims, it being understood that such changes in the precise embodiments of the herein disclosed invention are meant to be included as come within the scope of the claims.

DESCRIPTION OF THE INVENTION

Phosphonate monoesters may be described by the following formula:

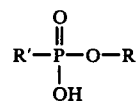

where R' is an alkyl, aryl or aralkyl, and R is an alkyl, aryl or aralkyl substituent which can be detected (either quantitatively by spectrophotometry, fluorometry, or potentiometry, or qualitatively by formation of a visible color and/or precipitate) on hydrolysis of the ester linkage.

As observed above, phosphonate monoesters are closely related to phosphate diesters which have the following formula:

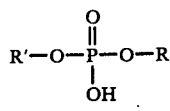

such phosphate diesters are known to be extremely important components of every living cell.

Both the phosphonate monoesters and the phosphate diesters possess only one titratable hydrogen which has a relatively low $pK_a$, between 1 and 2 depending upon the substituents. In addition, the phosphonate monoesters also mirror the phosphate diesters in chemical reactivity in that both are hydrolyzed in strongly acid solution, are very stable at neutral pH, and very slowly hydrolyzed in alkaline solution (see Cherbuliez, E., Hunkeler, L. F., and Rabinowitz, J., 1961 in Helv. Chim. Acta, Volume 44, page 1817).

Phosphonate monoesters contain a carbon-phosphorous bond, which is chemically quite stable (see Kosolapoff, G. M., Organophosphorus Compounds, Wiley, New York, Chapter 7, 1950), and has only a single hydrolyzable ester function. Phosphonate monoesters thus differ significantly from phosphate diesters in this regard, since phosphate diesters contain two hydrolyzable ester functions and do not contain a carbon-phosphorous bond.

Although they are rare compared to phosphates, phosphonates have been found in several living organisms. The distribution and biochemistry of naturally occurring phosphonates have been reviewed (see Rosenberg, H., 1973, in Form and Functon of Phospholipids, G. B. Ansell, J. N. Hawthorne, and R. M. C. Dawson, supra). Ed., Elsivier Scientific Publishing Company, Amsterdam, Chapter 12, and Kittredge, J. S. and Roberts, E., 1969, Science, Volume 164, page 37). Phosphonates have generally been subjected to such rigorous conditions during isolation that their physiological state of esterification could not be determined. Likewise, their function in living organisms has not been determined; it has been suggested that phosphonates are synthesized only by lower organisms, and are present in higher organisms only as a result of ingesting lower organisms which contain phosphonates (see Rosenberg, supra).

In contrast, phosphates are major constituents of every living cell. Phosphate diesters are among the most important chemical bonds known, for they are the structural basis of the nucleic acids, which maintain and transmit to succeeding generations genetic information in a chemical form. Other materials which contain phosphodiester bonds are intimately involved in regulation of cellular activities by hormonal action. Enzymes which make or break phosphodiester bonds are thus of considerable importance. Although many enzymes which hydrolyze phosphodiester bonds are known, those which hydrolyze nucleic acids sequentially form a terminus fit into one of the two broad classifications as observed above. The characteristics which define these two classes of phosphodiesterases are presented in Table I as follows:

Table I:

Definition of Phosphodiesterase I and Phosphodiesterase II According to Razell (1967).

| CHARACTERISTIC | PHOSPHODIESTERASE | |
|---|---|---|
|  | Type I | Type II |
| Usual Source | Snake venon | Bovine spleen |
| Cellular Location in Mammalian Tissue | Microsomes | Mitochondria |
| Type of Nuclease | Exonuclease | Exonuclease |
| pH Optimum | 9.2 | 5.9 |
| Effect of EDTA | Inactivation | None |
| Nucleic Acid Substrate Requirement | Free 3'-OH | Free 5'-OH |
| Product of Nucleic Acid Digestion | Nucleoside 5'-phosphates | Nucleoside 3'-phosphates |
| Artificial Substrate | Esters of 5'-TMP | Esters of 3'-TMP |

It will be shown below that the phosphonate monoesters which are the subject of this invention are hydrolyzed only by Type I phosphodiesterases.

GENERAL METHOD FOR SYNTHESIS OF PHOSPHONATE MONOESTERS

Monoesters of phosphonic acids are prepared by the displacement of chloride from an appropriate phosphonic acid dichloride by a phenol, usually either 2-naphthol or 4-nitrophenol, with pyridine as the solvent. After reaction for 3-4 hours at room temperature the solvent is removed on a rotary evaporator; the remaining ester chloride and dichloride are then hydrolyzed by the addition of water. The acid and ester are separated; the specific technique employed depends upon the nature of the compounds (see below). The acid-free ester is taken up in a polar organic solvent, either acetone or a mixture of chloroform and acetone, and precipitated as the salt by the addition of aqueous base, usually concentrated $NH_4OH$. The addition of the less polar diethyl ether facilitates the precipitation. The product is filtered, washed with fresh acetone, dried in vacuum dessicator, and stored below 0° C.

SEPARATION TECHNIQUES

All 2-naphthyl esters and 4-nitrophenyl cyclohexyl- and phenylphosphonate are extracted from water into benzene, maximized by the addition of concentrated HCl to the water layer; the benzene is then removed on a rotary evaporator. Under these conditions, paper chromatographic analysis shows that any acid present remains in the water layer. Separation of an aliphatic phosphonic acid (chloromethylphosphonate, 1- or 2-propylphosphonate, methylphosphonate) from its aromatic ester is achieved by a technique similar to the above but substituting chloroform for benzene, or by chromatograhic separation on a large (2.5 × 115 cm) column of polystyrene beads (Amberlite XAD-2) (Rohm and Haas, Philadelphia, PA). Under acid conditions (2% HOAc), the phosphonic acid appears in the void volume while the ester is retarded. The ester is then eluted with methanol. Solvents are removed by lyophilization.

EXAMPLE I

Synthesis of the 4-nitrophenyl monoester of phenylphosphonic acid

A solution of 10 gm 4-nitrophenol (0.072 mole) in 75 ml pyridine was added to 10 ml (0.071 mole) phenylphosphonic dichloride in 125 ml pyridine. After reaction for 4 hr at room temperature, solvent was removed on a rotary evaporator.

To the residue 75 ml H$_2$O was added and the mixture was extracted 5 tmes with 150 ml benzene. Extraction of the ester into the benzene layer is maximized by the addition of HCl to the water layer. Benzene fractions containing free phenyl-phosphonic acid in addition to monoester, as determined by paper chromatographic analysis with 2-propanol:H$_2$O:NH$_4$OH (80:20:0.2) as irrigant, were reextracted with 50 ml of approximately 0.5 M HCl.

Benzene was evaporated off on a rotary evaporator, the residue was taken up in approximately 100 ml of acetone, and concentrated NH$_4$OH was added in slight molar excess. The ammonium salt of 4-nitrophenyl phenylphosphonate crystallizes immediately and maximum yield is obtained on addition of a 3-fold volume of diethyl ether. The crystals were washed with fresh acetone, dried in a vacuum dissicator and stored below 0° C. 12.13 gm (57% yield) was obtained.

EXAMPLE II

Synthesis of the 4-nitrophenyl ester of 1-propylphosphonic acid

A solution of 2.365 gm (.017 mole) 4-nitrophenol in 20 ml pyridine was added to 2.12 ml (.017 mole) propylphosphonic dichloride in 30 ml pyridine. After reaction for 4 hr at room temperature, solvent was removed on a rotary evaporator.

To the residue 20 ml H$_2$O was added, and the mixture was extracted 3 times with 30 ml chloroform. Extraction of the ester into the cloroform layer is maximized by the addition of HCl to the water layer. Chloroform fractions containing free 1-propylphosphonic acid in addition to monoester, as determined by paper chromatographic analysis with 2-propanol:H$_2$O:NH$_4$OH (80:20:0.2) as irrigant, were re-extracted with 20 ml of approximately 0.5 M HCl.

Chloroform was evaporated off on a rotary evaporator, the residue was taken up in 15–20 ml acetone and concentrated NH$_4$OH was added in slight molar excess. The ammonium salt of 4-nitrophenyl 1-propylphosphonate crystallizes immediately and maximum yield is obtained on addition of a three-fold volume of diethyl ether. The crystals were washed with fresh acetone, dried in a vacuum dissicator, and stored below 0° C. 2.37 gm (53% yield) was obtained.

EXAMPLE III

Synthesis of the 2-naphthyl monoester of phenylphosphonic acid in the absence of dimethyl formamide A solution of 5.09 (0.02145 mole) 2-naphthol in 20 ml pyridine was added to 1 ml (0.00715 mole) phenylphosphonic dichloride in 30 ml pyridine. After reaction for 4 hr at room temperature, solvent was removed on a rotary evaporator.

To the residue 20 ml H$_2$O was added and the mixture was extracted 3 times with 30 ml benzene. Extraction of the ester into the benzene layer is maximized by the addition of HCl to the water layer. No free phenylphosphonic acid was detected, on paper chromatographic analysis with 2-propanol:H$_2$O:NH$_4$OH (80:20:0.2) as irrigant, in any of the benzene layers when the initial reactant concentrations are in a phenol:dichloride ratio of 3:1.

Benzene was evaporated off on a rotary evaporator, the residue was taken up in approximately 20 ml of acetone and concentrated NH$_4$OH was added in slight molar excess. The ammonium salt of 2-naphthyl phenylphosphonate crystallizes immediately and maximum yield is obtained on addition of a 3-fold volume of diethyl ether. The crystals were washed with fresh acetone, dried in a vacuum dissicator, and stored below 0° C. 0.90 gm (42.6% yield) was obtained.

Summary of Syntheses of Phosphonate Monoesters

The following table presents a listing of the phosphonate monoesters which have been prepared, along with the separation technique utilized, and the yield of monoester isolated:

Table II:

Summary of Syntheses of Phosphonate Monoesters.

| COMPOUND | SEPARATION TECHNIQUE[a] | YIELD[b] % | R$_f$[h] |
|---|---|---|---|
| 4-nitrophenyl phenylphosphonate | C$_6$H$_6$ | 20[c,d]; 58 | .73 |
| 2-naphthyl phenylphosphonate | C$_6$H$_6$ | 72[c]; 78 | .75 |
| 4-nitrophenyl cyclohexylphosphonate | C$_6$H$_6$ | 10[e] | .80 |
| 2-naphthyl cyclohexylphosphonate | C$_6$H$_6$ | 40 | .80 |
| 4-nitrophenyl propylphosphonate | XAD-2; CHCl$_3$ | f; 53 | .74 |
| 2-naphthyl propylphosphonate | C$_6$H$_6$ | 59 | .75 |
| 4-nitrophenyl 2-propylphosphonate | CHCl$_3$ | 51 | .75 |
| 2-naphthyl 2-propylphosphonate | C$_6$H$_6$ | 60 | .76 |
| 4-nitrophenyl chloromethylphosphonate | XAD-2 | f | .62 |
| 2-naphthyl chloromethylphosphonate | C$_6$H$_6$ | 44 | .68 |
| 4-nitrophenyl methylphosphonate | XAD-2; CHCl$_3$ | f,g | .59 |
| 2-naphthyl methylphosphonate | C$_6$H$_6$ | 64 | .63 |

[a]C$_6$H$_6$ refers to benzene extraction and CHCl$_3$ to chloroform extraction of water layer. XAD-2 refers to chromatography on polystyrene beads
[b]Percentage calculated on basis of limiting component. All compounds were chromatographically pure.
[c]Ratio phenol : dichloride was 1:3 but acid not added to maximize extraction into benzene. Ester isolated in acid rather than in salt form.
[d]Anal.: Calculated for C$_{12}$H$_{10}$NO$_5$P:
C, 51.62; H, 3.61; N, 5.01; P, 11.09; FW 279.1.
Found: C, 51.42; H, 3.62; N, 4.91; P, 11.00; FW 280.
[e]Compound was colloidal and would not separate well.
[f]Yield not calculated for XAD-2 eluates.
[g]Incompletely separated from CHCl$_3$ layer; yield not calculated.
[h]On ascending paper chromatography using 2-propanol:H$_2$O:NH$_4$OH (80:20:0.2).

All except 4-nitrophenyl methylphosphonate (Behrman et al., 1970), as far as is known, are compounds whose preparations are previously unreported in the literature.

The yields of the preparations were good with the exception of the 4-nitrophenyl ester of cyclohexyl- and methylphosphonate. These lowered yields are probably due to incomplete isolaton of the product. The yields of the 4-nitrophenyl esters were somewhat lower than those of the 2-naphthyl esters in all cases.

The use of hydrophobic chromatography for the separation of the monoester from the acid is less convenient than the extraction procedure since it requires removal of the large volumes of solvent required to extract the ester from the column. On the other hand, the chromatographic procedure is a more complete one-step separation of the acid and ester. Some of the organic extracts contained detectable acid which required repeated extraction with water for complete removal.

The isolation of the phosphonate monoesters as ammonium salts is quite useful. The compounds appear to be much more stable and also more water soluble than the corresponding acid. Solutions of the ammonium salt of 4-nitrophenyl phenylphosphonate are stable in concentrations to 0.1 M for several weeks at 0°–4° C.

Effect of Relative Reactant Concentrations on Yield

The effect of varying the relative concentration of phenylphosponic dichloride and 2-naphthol on the yield of 2-naphthyl phenylphosphonate isolated is shown in Table III as follows:

Table III:

| Effect of Reactant Concentration on Yield. | | |
|---|---|---|
| RELATIVE CONCENTRATION OF REACTANT | | YIELD[a] |
| Dichloride | Phenol | % |
| 3 | 1 | 94.9 |
| 2 | 1 | 82.3 |
| 1 | 1 | 78.6 |
| 1 | 2 | 49.9 |
| 1 | 3 | 42.6 |

[a]Yield is calculated on the basis of the limiting component and is not corrected for any waters of hydration.

Yield is maximal when the ratio of 2-naphthol to phenylphosphonic dichloride is 1:3, however a ratio of 1:1 was employed in most syntheses due to the relative scarcity of certain dichlorides. The decreased yield of monoester with increasing phenol to dichloride ratios may be explained by increased formation of phosphonate diester.

It is well known that dimethylformamide will react with phosphorusoxychloride. Indeed this is the basis for the use of the phosphorusoxychloride in the Vilsmeier reaction (see Feiser, L. F. and Feiser, M., 1961 Advanced Organic Chemistry, Reinhold Publishing Company, New York, page 822). Table IV (which follows) shows that incubation of phenylphosphonic dichloride with a stoichiometric or a two-fold amount of DMF prior to the addition of three-fold amount of 2-naphthol increases the yield of 2-naphthyl phenylphosphonate isolated, suggesting that if the decreased yield of monoester obtained at high phenol:dichloride ratios is due to the formation of diester, the addition of DMF serves to prevent or at least to restrict the formation of diester.

Table IV:

| Effect of DMF and Yield at High Ratios of Phenol : dichloride. | | |
|---|---|---|
| RATIO Phenol : dichloride | DMF | YIELD[a] % |
| 3:1 | 0 | 42.6 |
| 3:1 | 1 | 80.5 |
| 3:1 | 2 | 85.6 |

[a]Yield is calculated on the basis of the limiting component and is not corrected for any waters of hydration.

EXAMPLE IV

Syntheses of 2-naphthyl monoester of phenylphosphonic acid in the presence of dimethyl formamide To a solution of 1.0 ml (.00715 mole) phenylphosphonic dichloride in 30 ml pyridine was added 0.55 ml (.00705 mole) or 1.10 ml (.0141 mole) dimethylformamide (DMF). After reaction for 15 min. 3.09 gm (.02145 mole) 2-naphthol was added and let react for 4hr. The solvent was removed on a rotary evaporator, and the ammoniium salt of 2-naphthyl phenylphosphonate was isolated exactly as in Example III. Yields were 1.7066 gm (80.5%) and 1.8157 gm (85.6%) respectively.

The mechanism by which DMF interacts with the dichloride may involve displacement of one of the chlorides from the phosphonic dichloride leaving only one chloride with which the napthol can interact. A mechanism analogous to that thought to occur in the Vilsmeier reaction might be operative, the suggested mechanism for the prevention of phosphonate diester formation by incubation of phosphonyl dichloride with DMF prior to addition of phenol being as follows:

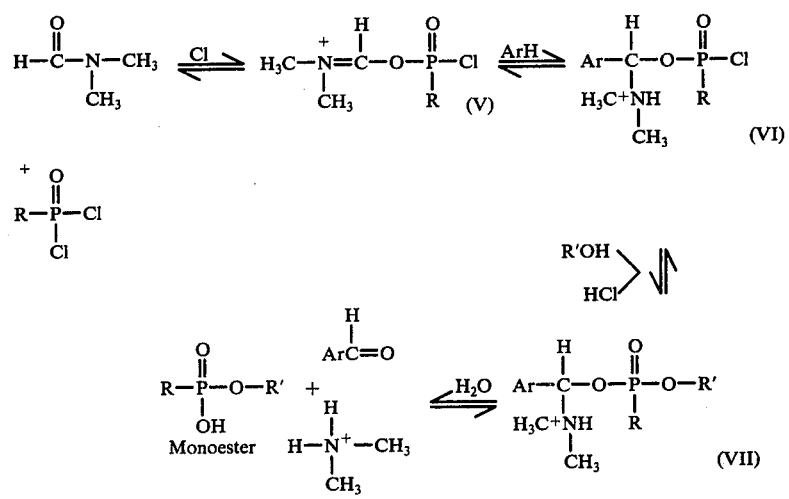

Thus DMF reacts with the phosphonic dichloride to form a complex (V) which combines with the aromatic solvent to produce a second complex (VI), which on the addition of phenol, could only react at one site (VII). This compound on addition of water would hydrolyze to yield the desired monoester. Good yields of monoester have been obtained from reaction mixtures containing up to 50% DMF, suggesting that the reaction of DMF with phosphonic dichloride occurs at only one site.

Brooks, R. J. and Bunton, C. A., in 1973 in the Journal of Organic Chemistry, Volume 38, page 1614, noted a similar effect by dimethyl sulfoxide on the reaction of phenylphosphonic dichloride with methanol. Although the general effect is the same, the detailed mechanism by which one chlorine is blocked to reaction with the alcohol or phenol by dimethyl sulfoxide is most certainly different from that involving DMF.

EXAMPLE V

Assay in solution

Enzymic hydrolysis of 4-nitrophenyl esters is quantitated spectrophotometrically by the appearance of the 4-nitrophenolate ion at 400 nm ($\epsilon = 18,320$ M$^{-1}$ cm$^{-1}$, pK 7.15) (see Kezdy, F. J. and Bender, M. L., 1962, Biochemistry, Volume 1, page 1097), either continuously above pH 7.0 or discontinuously by raising the assay mixture to pH 9 and inactivating the enzyme by the addition of two volumes of 1 M NaHCO$_3$, 10 mM Na$_3$PO$_4$, 10 mM Na$_2$EDTA. Standard assay conditions are 1 mM 4-nitrophenyl phenylphosphonate, 0.1 M Tris, pH 8.0, 30° C.

EXAMPLE VI

Typical assay in polyacrylamide gel

A polyacrylamide gel, on which enzymic activity sufficient to hydrolyze 1 mM 4-nitrophenyl phenylphosphonate in 0.1 M Tris, pH 8.0, at a rate of at least 0.01 μmole 4-nitrophenol produced per min has been applied and electrophoresed according to a procedure as shown by Davis, B. J. (1964, Ann. N.Y. Acad. Science, Volume 121, page 404), is immersed in a solution containing 5-10 mM 2-naphthyl phenylphosphonate and 0.1% Fast Garnet GBC Salt (Sigma Chemical Company). After 10-30 min a red band of the azo dye formed by the freed 2-naphthol and the diazonium salt appears at the site of type I phosphodiesterase activity.

EXAMPLE VII

Distribution of Enzymes Capable of Hydrolyzing Phosphonate Monoesters

Enzymes which hydrolyze phosphonate monoesters are widely distributed in nature as shown in Table V as follows:

Table V:

Phosphonate Monoesterase Activity of Several Plant and Animal Tissues

| SOURCE | ACTIVITY[a] (n moles min$^{-1}$g$^{-1}$) | SOURCE | ACTIVITY[a] (n moles min$^{-1}$g$^{-1}$) |
|---|---|---|---|
| Algae | 2.0 | E. coli | 33.0 |
| Mushroom | 1.8 | Sea Urchin | 0.3 |
| Moss | 0.5 | Crayfish | 2.0 |
| Fern frond | 0.9 | Frog intestine | 1.7 |
| Ginko leaf | 0.4 | Fish intestine | 2.8 |
| Corn leaf | 1.0 | Chicken intestine | 3.3 |
| Spinach leaf | 1.4 | Rabbit ileum mucosa | 800 |
|  |  | Chicken intestinal mucosa | 1770 |
|  |  | Frog intestinal mucosa | 1020 |

[a]Weighed tissue was homogenized in 0.1 M Tris. pH 8.0, in a Warning blendor, centrifuged, and 0.1 ml of the supernatant assayed under standard conditions. Activity is expressed per gram fresh or thawed weight of tissue.

Vetebrate intestinal mucosa is an especially rich source of this enzyme.

EXAMPLE VIII

Comparison of Kinetic Parameters of Hydrolysis of Phosphonate Monoesters and Conventional Phosphodiesterase Substrates As determined with a purified bovine intestinal phosphodiesterase, as shown in Table VI as follows:

Table VI

Kinetic Parameters for Hydrolysis of Nucleotide Esters and Related Compounds by Purified Phosphonate Monoesterase Activity of Calf Intestinal Mucosa.[a]

| Compound | $V_{max}$ (μmoles min$^{-1}$mg$^{-1}$) | $K_m$ |
|---|---|---|
| 4-nitrophenyl phenylphosphonate | 744 | 11.1 |
| bis-(4-nitrophenyl)phosphate | 24 | 0.85 |
| 4-nitrophenyl 5'-TMP | 270 | .043 |
| 4-nitrophenyl 3'-TMP | 1 | — |

[a]Production of 4-nitrophenol was measured continuously at 400 nm in 0.1 M Tris pH 8.0 at 30° C.

phosphonate monoesters are hydrolyzed at a maximal rate which is three times faster than the corresponding maximal rate for the best conventional phosphodiester substrate, and thirty times faster than the rate for the commonly employed phosphodiester, bis-(4-nitrophenyl) phosphate. However, the affinity of the enzyme (inversely proportional to the $K_m$ values) appears to be lower for the phosphonate monoesters than for phosphodiesters.

EXAMPLE IX

Phosphonate Monoesterase Activity of Human Serum

Over 450 samples of human serum have been assayed for their capacity to hydrolyze 4-nitrophenyl phenylphosphonate. All samples contain this activity; in approximately 97% of the samples the level of activity is between 8 and 27 nmoles min$^{-1}$ ml$^{-1}$. The samples which lie outside this range may show significant correlations with a clinical condition.

EXAMPLE X

Use of Phosphonate Monoesters for Distinguishing between Phosphodiesterase Type I and Type II Table VII is a comparison of Type I and Type II Phosphodiesterase as follows:

Table VII:

Comparison of Type I and II Phosphodiesterases for Activity Against Phosphonate Monoesters and Conventional substrates

| | Activity (nmoles min⁻¹ mg⁻¹) | | |
|---|---|---|---|
| Type I enzymes | phenylphosphonate | 5'-TMP | 3'-TMP |
| Bovine Intestine | 38,900 | 65,700 | .569 |
| Snake Venon | 1230 | 4570 | 1.9 |
| Type II enzyme | | | |
| Bovine spleen | 1.0 | 6.9 | 168 |

Substrates were 1 mM solutions of the 4-nitrophenyl esters of the above compounds.

The data presented in Table VII demonstrates that phosphonate monoesters are good substrates for phosphodiesterases of the Type I specificity (see Table I) but not the Type II specificity. Only the activity of the Type I enzymes is measured with phosphonate monoesters. The type of a phosphodiesterase can thus be determined by its activity against phosphonate monoesters.

As seen from the structure of phosphonate monoesters as above set forth, both the substituent directly attached to the phosphorous atom and the esterified substituent can be varied at will. Present indications are that variations in the former result in differences in both the maximum rate of enzyme hydrolysis and the affinity of the enzyme for the material, while variations of the esterified substituent affect only the affinity. For most purposes it would not be necessary to employ as enzyme substrates several phosphonate monoesters differing only in the substituent directly attached to the phosphorous atom, although for certain mechanistic studies this would be desirable.

It is probably more desirable to have available a variety of esterified substituents. For convenience in spectrophotometric assays, these should be chromogenic (absorb light more strongly upon hydrolysis of the ester linkage). The synthesis of two such classes has been described, the 4-nitrophenyl and 2-naphthyl esters, and a catechol ester has been utilized spectrophotometrically. Other chromogenic or fluorogenic phosphonate monoesters which could be synthesized and utilized in a manner analogous to that described above include esters of phenolphthalein, thymolphthalein, 4-methylumbelliferol, phenol, 3-hydroxyflavone (Land, D. B. and Jackim, E., 1966, Anal. Biochem, Volume 16, page 481), 5-bromo-4-chloro-3-hydroxyindole (Epstein, E., Wolf, P. L., Horowitz, J. P. and Zak, B., 1967, Am. J. Clin. Path., Volume 37, page 530), and 5-iodoindoxyl, 5-iodoinol-3-yl, and 5-nitroindoxyl monoesters of phosphonic acids (Tsou, et al., 1972, J. Med. Chem. Volume 15, page 1221, and Rabiger, et al., 1970, J. Heterocyclic Chem., Volume 7, page 307). This invention is not meant to be limited, however, to the specific esters set forth and is not meant to preclude unmentioned analogous esters. For example, replacement of oxygen by sulfur in the ester linkage gives esters of two forms as follows:

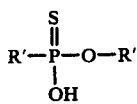 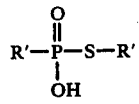

While these compounds have not been specifically tested as phosphodiesterase substrates, it is possible that their use will result in similar or greater advantages than the oxygen-containing analogs described above.

The present invention is felt to provide an advantage of ease of preparation. The use of dimethylformamide makes it impossible to form the undesired diesters of phosphonates, thus maximizing yields of monoester.

The use of phosphonic dichlorides for synthesis is also felt to offer an advantage since it makes it unnecessary to employ expensive and toxic carbodiimide coupling reagents.

The cost of preparing phosphonate monoesters is far less than the cost of preparing chromogenic esters of nucleotides, which must first be purified from natural sources and then esterified by more exotic chemistry and therefore adds a further advantage.

Stability is still another advantage — the 4-nitrophenyl ester of phenylphosphonate is stable indefinitely as the dry ammonium salt. It is much more stable in solution than is 4-nitrophenyl phosphate.

Still another advantage is that the phosphonate monoesters are not inferior to conventional substrates but are hydolyzed at rates comparable to the esters of nucleotides. These rates are far superior to those obtained with bis-(4-nitrophenyl)phosphate.

Because phosphonate monoesters contain only one hydrolyzable ester function, a further advantage is that there is no ambiguity in interpreting the rate obtained. In contrast, when bis-(4-nitrophenyl)phosphate is used as substrate, one of the products of phosphodiesterase action is 4-nitrophenyl phosphate, which is a good substrate for any alkaline or acid phosphatase which may be present. Thus, the diester may release two moles of 4-nitrophenol for every mole of diester cleaved. The use of phosphonate monoesters avoids this possibility.

The following applications have been reduced to practice:

Assays of phosphodiesterase Type I in solution (Example V, IX);

Assays of phosphodiesterase Type I on polyacrylamide gels after electrophoresis (Example VI); and Distinguishing between phosphodiesterase Type I and Type II (Example X);

while the following applications have been conceived but not reduced to practice:

Use of phosphonate monoesters as substrates for phosphodiesterase Type I in histochemical assays: and Assays of phosphodiesterase Type I on starch slabs or other means of support.

From the foregoing, it can be seen that this invention provides novel formulations of phosphonate monoesters, as well as uses and methods of such monoesters as substrates for phosphodiesterase enzymes.

What is claimed is:

1. A substrate for phosphodiesterase enzymes, said substrate being a biologically active phosphonate monoester that is hydrolized by said phosphodiesterase enzymes with said phosphonate monoester being selected from the group consisting of 4-nitrophenyl phenylphosphonate, 2-naphthyl phenylphosphonate, 4-nitrophenyl cyclohexylphosphonate, 2-naphthyl cyclohexylphosphonate, 4-nitrophenyl 1-propylphosphonate, 2-naphthyl 1-propylphosphonate, 4-nitrophenyl 2-propylphosphonate, 2-naphthyl 2-propylphosphonate, 4-nitrophenyl chloromethylphosphonate, 2-naphthyl chloromethylphosphonate, and 2-naphthyl methylphosphonate.

2. A method for synthesising phosphonate monoesters, said method comprising:
providing a phosphonic acid dichloride capable of being reacted to form a monoester monochloride in an aromatic solvent;
adding dimethylformamide in an amount up to about twice that of said phosphonic acid dichloride to said phosphonic acid dichloride in said aromatic solvent to prevent formation of diester;

adding 2-naphthol or 4-nitrophenol in an amount up to about three times that of said phosphonic acid dichloride after the additiion of said dimethylformamide so that an interaction occurs with said phosphonic acid dichloride to displace chloride therefrom and form a monoester monochloride;

hydrolyzing the monochloride and any remaining dichloride; and separating the monoester from the free phosphonic acid.

3. The method of claim 2 wherein said monoester monochloride is formed by reacting the phosphonic acid dichloride and 2-naphthol or 4-nitrophenol with pyridine for a period between 3 and 4 hours at room temperature, and then removing the pyridine on a rotary evaporator.

4. The method of claim 2 wherein a salt is formed by adding an aqueous base to the monoester and precipitating the same by the addition of a polor non-aqueous solvent.

5. The method of claim 4 wherein said aqueous base is concentrated $NH_4OH$.

6. The method of claim 2 wherein said phosphonate monoester formed is filtered, washed with acetone, and dried by a vacuum dessicator prior to storage at a temperature below 0° C.

* * * * *